United States Patent [19]

Cosman

[11] 4,281,666
[45] Aug. 4, 1981

[54] SINGLE DIAPHRAGM PRESSURE-BALANCED TELEMETRIC PRESSURE SENSING SYSTEM

[76] Inventor: Eric R. Cosman, 872 Concord Ave., Belmont, Mass. 02178

[21] Appl. No.: 895,953

[22] Filed: Apr. 13, 1978

Related U.S. Application Data

[62] Division of Ser. No. 697,951, Jun. 21, 1976, abandoned.

[51] Int. Cl.³ .............................................. A61B 5/00
[52] U.S. Cl. ..................................... 128/748; 73/722; 128/660
[58] Field of Search ............... 128/673, 675, 748, 660; 73/701, 708, 716–719, 722

[56] References Cited

U.S. PATENT DOCUMENTS

| | | | |
|---|---|---|---|
| 3,034,356 | 5/1962 | Bieganski et al. | 128/748 |
| 3,038,465 | 6/1962 | Allard et al. | 128/675 |
| 3,625,199 | 12/1971 | Summers | 128/748 |
| 3,720,108 | 3/1973 | Freitag | 73/722 |
| 3,722,373 | 3/1973 | Beach et al. | 73/716 X |
| 3,724,275 | 4/1973 | Battaglini et al. | 73/716 |
| 3,727,463 | 4/1973 | Intraub | 73/398 R |
| 3,757,770 | 9/1973 | Brayshaw et al. | 128/748 X |
| 3,853,117 | 12/1974 | Murr | 128/748 X |
| 3,859,484 | 1/1975 | Nelson | 73/716 X |
| 3,943,915 | 3/1976 | Severson | 73/406 X |
| 4,014,319 | 3/1977 | Faure | 128/748 |
| 4,026,276 | 5/1977 | Chubbuck | 128/653 |
| 4,067,241 | 1/1978 | Corbett | 73/717 |
| 4,124,023 | 11/1978 | Fleischmann et al. | 128/748 |
| 4,127,110 | 11/1978 | Bullara | 128/748 |
| 4,141,348 | 2/1979 | Hittman | 128/748 |

OTHER PUBLICATIONS

Collins, C. C., *IEEE Trans. on Bio.-Med. Engng.*, vol. 14, No. 2, Apr. 1967, pp. 74-83.
Atkinson, J. R., et al., *Journ. of Neurosurgery*, 1967, vol. 27, No. 5, pp. 428-432.

*Primary Examiner*—Kyle L. Howell
*Attorney, Agent, or Firm*—Richard J. Birch

[57] ABSTRACT

A differential pressure sensing device is fully implanted in the body of a patient to monitor internal pressure such as intracranial pressure. A movable element in the sensor communicates on one side with the internal pressure to be measured and on the other side with an external pressure which is applied by an external pressurizer-control system and which is communicated to the sensor through the intact skin. An imbalance of the two opposing pressures causes a displacement of the movable element which changes a physical characteristic of the sensor, such as the resonant frequency of a tuned L-C circuit. This change is detected outside the body by an external detection system, such as a frequency swept radio frequency oscillator. The external pressure is varied until the external detector senses that the pressures are balanced on the movable element, at which point the external pressure equals the internal pressure, and the former is measured and read out.

40 Claims, 10 Drawing Figures

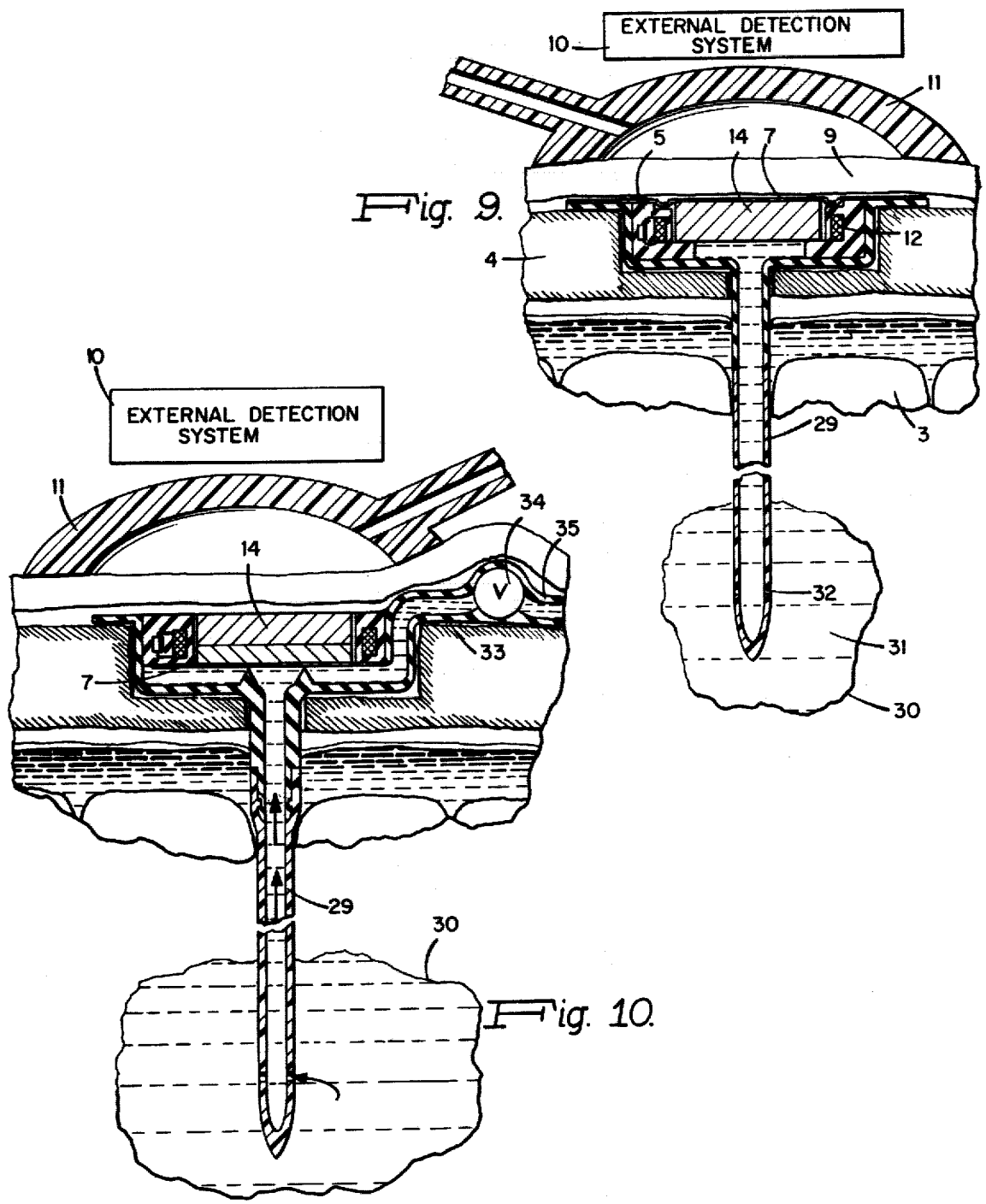

SINGLE DIAPHRAGM PRESSURE-BALANCED TELEMETRIC PRESSURE SENSING SYSTEM

CROSS REFERENCE TO RELATED APPLICATION

This application is a divisional application of Ser. No. 697,951, filed June 21, 1976, now abandoned, by Eric R. Cosman for A Pressure-Balanced Telemetric Pressure Sensing System and Method Therefore.

BACKGROUND OF THE INVENTION

The invention relates to the precision measurement and monitoring of pressures in a confined region and particularly in a living body, such as intracranial pressure in the head, by means of a long-term totally implanted pressure sensor which undergoes a conformational change with pressure and which is coupled through the skin by electromagnetic, acoustic, or mechanical transmission to an external device which detects that change and interprets the pressure. The invention refers additionally to a device which is automatically barometric compensated, has immediate zero point reference check, can be made passive, and is insensitive to barometric or temperature changes.

At the present time there is no such wireless device available for general clinical or research purposes. The uses for such a device in neurosurgery would be immediate in the management of intracranial hypertension, monitoring of intracranial pressure in all cases of intracranial neurosurgery and head trauma, long-term diagnostics for evidence of tumor recurrence, and management of hydrocephalus.

All devices previously proposed have significant shortcomings which make them impractical for widespread, safe, accurate, reliable, and longterm use as intracranial pressure monitors. Most designs involve a tube or wire connection through the skin to an external device, and since this greatly increases the chance of infection and electrical shock to the patient and reduces the patient's mobility, they are hazardous and impractical. Of the devices which are wireless and fully implanted, they usually involve a sealed inner volume containing a fixed amount of gas, this being housed in a flexible container which deflects under pressure. The major problems with this design aspect are the following: liquids and gases will inevitably diffuse through the membranes and walls of the container causing steady drift of the zero-point reading, and causing an unpredictable error in the device's calibration; changes in barometric pressure will cause significant variations in the body pressure relative to the fixed volume pressure and thus the device's pressure readout must be corrected for barometric pressure changes in the external detection system; a trapped volume of significant size could make it dangerous for a patient to experience atmospheric pressure change, such as those found in air travel, for fear of rupturing the device; and temperature changes in the patient will cause changes in the trapped volume and resultant errors in the pressure reading. Previous totally implanted designs provide no means to check their zero-pressure calibration after implantation and thus no means to determine diffusion or temperature drifts in the readings nor any check of the proper function of the device, which is essential for long and short-term implantation. Most previous designs are of complex construction involve high tolerance parts and assembly, and are not amenable to calibration standardization; all of which make them expensive, inaccurate, and unsuitable for simple and general application.

Accordingly, some of the principal objects of the present invention are the following:

(1) To provide a pressure detector which can be implanted for an indefinite period under a fully intact skin with no wire or tube connections to the exterior so as to reduce infection and electrical shock hazard, and to read pressures in inaccessible spaces in the body, such as intracranial pressure, with an accuracy of 5 to 10% or better.

(2) To eliminate or make insignificant all inaccuracies, and dependencies on a trapped volume of gas or fluid in the device to make the pressure readings insensitive to drifts from membrane permeability, barometric change and temperature variation, and to eliminate the hazard of rupturing the device during air travel.

(3) To provide automatic barometric compensation as a built-in feature of the implanted device.

(4) To provide a means of easily and instantly checking the zero-pressure calibration of the device.

(5) To provide a sufficiently fast dynamic response to enable observation of variations in the body pressure due to heart rate, respiration, and any other physiological changes.

(6) To allow a simple calibration standardization of the implant.

(7) To allow the implanted device to be of simple, passive, compact, and low cost construction so as to be implanted permanently and to function properly for indefinitely long periods.

(8) To make the system amenable to telemetry over long distances so as to monitor pressures in a freely moving patient.

SUMMARY OF THE INVENTION

The invention enables the precision measurement of pressure inside the living body without a break through the skin or wires or tubes through the skin and involves a novel differential pressure sensing device fully implanted in the body, an external detection system which can interrogate the implanted sensor in the body, an external pressurizing system which can control and measure pressure which is applied to the skin in the region of the implanted sensor, and a means of displaying and recording the pressure applied by the external pressurizing-control system. The principle of operation of the invention is the following: the fully implanted sensor, which is covered by a completely intact skin, contains a movable element which feels the internal bodily pressure to be measured on one side and an external pressure applied through the intact skin over the sensor by the pressurizing-control system on the other side, so that its equilibrium position corresponds to a balancing or equality of the two pressures. This equilibrium condition or balanced position of the movable element is detected with an external detection system by means of electromagnetic, acoustic, radiation, mechanical, or other methods of coupling across the skin to the implanted sensor. The externally applied pressure on the skin, which corresponds to the internal body pressure when the balance condition is attained, can be measured with high precision and may be controlled manually or automatically and varied until the balanced condition is detected. The implanted sensor can have a built-in fiducial point corresponding to the pressure balanced position of the movable element which can be checked at any time by pressing manually on the skin covering the sensor, thereby bringing the movable element to the fiducial position and allowing the external detection system to be adjusted or "zeroed" relative to it. In operation, a deviation from this reference position caused by a difference in pressures across the implanted sensor is detected by external detection system and an associated error signal can be used to increase or decrease the externally applied pressure so as to equalize the internal and external pressures. In this way the external pressurizing-control system can be made to track variations in the internal pressure to be measured.

A specific illustration of this invention will be given in which the implanted sensor contains a passive L-C tank circuit, the inductance, capacitance, or both of which are pressure dependent. The resonant frequency of this circuit is thus pressure dependent and is detected by the external detection system in order to determine if the system is or is not in the pressure balanced condition, which information may be used to provide an error signal to the external pressurizing-control system. The external detection system in this case is coupled electromagnetically to the implanted sensor and may embody a swept frequency, energy dip oscillator to detect the sensor's resonant frequency. Several other ways of implementing this invention concept will be cited. Several illustrative embodiments of the invention will be shown which have application in measuring and monitoring intracranial pressure.

The present invention has all of the novel and unique advantages of the wireless and tubeless pressure measuring device described in my copending divisional patent application Ser. No. 895,954 filed on April 13, 1978 and, in addition, has several other novel features and differences. Like the said other invention, the present invention makes use of pressure transmission through the fully intact skin and does not compress a trapped volume of gas in the sensor, and this eliminates problems of zero-point calibration drift, barometric compensation, and rupture hazard. However, the said other invention uses only atmospheric external pressure and relies further on a spring in the sensor to provide a calibrated displacement of a movable element in the sensor for a given internal pressure to be measured. In contrast, the present invention eliminates the spring force by applying an externally controlled pressure to the sensor across the skin and thus makes the pressure measurement at only one position corresponding to zero displacement of the movable element in the sensor; thus placing the burden of pressure calibration in the external equipment and eliminating inaccuracies due to surface tension effects at non-zero displacements. The method of the present invention has the resulting advantages of greater accuracy, range of pressure measurement, linearity, and simplicity of sensor construction.

DESCRIPTION OF THE DRAWINGS

Further objects, advantages, and aspects of the present invention can be gained from the following detailed description, illustrative drawings, and various embodiments and implementations. Illustrations will be given for measuring intracranial pressure although uses in other parts of the body are possible. In the following drawings similar reference characters represent similar parts.

FIG. 9 shows a pressure sensor similar to that of FIG. 2 with specific design variations and an attached catheter.

FIG. 10 shows a combination of the present invention with a catheter and a fluid shunt valve for control of hydrocephalus.

FIG. 1 illustrates the major elements of the implanted pressure sensor, used in this example as a monitor of epidural intracranial pressure if the dural membrane 1 is intact or of cerebrospinal fluid 2 pressure that surrounds the brain 3 if the dura 1 is cut. The sensor, which is inserted into a burrhole drilled in the skull 4 comprises a housing 5 which has a through opening in it in which moves a movable element 6. A flexible diaphragm 7 attached to the housing 5 communicates on one side with the intracranial pressure $p_{ICP}$ inside the skull and communicates on the other side with the external pressure $p_{EXT}$ in the region 8, which is transmitted across the intact scalp 9. Diaphragm 7 is also attached to movable element 6. By this system a difference $\Delta p = p_{ICP} - p_{EXT}$ will cause a force imbalance ohn element 6 and diaphragm 7 and for example if $\Delta p$ is positive that net force will cause the movable element 6 and flexible diaphragm 7 to be displaced upward. If $p_{EXT}$ is then increased so as to balance the pressure $p_{ICP}$, i.e. $p_{EXT} = p_{ICP}$, then $\Delta p = 0$ and the movable element 6 is restored to its balanced position. The balanced position of movable element 6 relative to the body 5 is indicated by a shoulder stop in FIG. 1, but other physical or electromagnetic fiducials are possible. A displacement of 6 relative to 5 can be made to cause changes in some physical, electrical, or magnetic characteristic of the sensor. Those changes can be detected by an external detection system 10 which is coupled to the implanted sensor by electromagnetic, acoustic, or other means across the skin, but not through the skin as by a tube or wire. The balance position may be predetermined and calibrated during construction so that it can be easily recognized after implantation by some known value of an eleectrical or mechanical characteristic of the sensor. Alternatively, with a mechanical stop to interrupt the downward movement of 6 relative to 5 as in FIG. 1, pressing on the skin just above diaphragm 7 will bring the sensor into its balanced condition and provides an instant zero-point calibration and check of the sensor and detector systems $\Delta p = 0$ reference long after implanatation. In operation external detector 10 interrogates the implanted sensor and determines if a balanced condition, $\Delta p = 0$, or imbalanced condition, $\Delta p \neq 0$, exists in the sensor. With elevating intracranial pressure $\Delta p$ will become more positive temporarily. This will be detected by 10 and $p_{EXT}$ will be increased by an external pressurizer attached to the pressure applicator 11 until detector 10 detects a balanced condition $=0$ at which point $p_{EXT} = p_{ICP}$ and may be recorded or read out. No particular calibration of $\Delta p$ versus displacement of element 6 relative to the frame is necessary although this may be built-in by spring loading 6, for added flexibility of measurement. The pressure balance method described here reduces the degree of complexity of the transsensor construction to only that necessary to detect deviations from a balance position rather than a calibrated pressure versus displacement characteristic. Thus, the burden of accurate pressure detection instrumentation lies external to the body where it is easily implemented. Common implementations of the coupling of the motion of 6 to the external detector 10 are by use of a passive L-C circuit; this will be discussed below.

Referring to FIG. 2, a specific embodiment of the basic invention concepts of FIG. 1 is shown. The cylindrical body 5 comprises an insulating plastic such as nylon or "Lexan" and has an upper flange so that it seats in a standard burr hole in the skull 4. A fixed coil 12 and capacitor 13 are embedded in the body 5 to form a parallel L-C tank circuit. A magnetic slug 14 moves in a cylindrical hole through the body 5 and is attached to a coaxial cylinder 15, made of a non-magnetic material to the movable element 6 of FIG. 1. The diaphragm 7 is made of thin flexible plastic material, may be convoluted for added flexibility, sealed to the body 5, and contact the end of cylinder 14 or 15. Cylinders 14 and 15 end-for-end symmetry such that $p_{ICP}$ is felt on one end, $p_{ATM}$ is communicated through the intact skin is felt on the other end, and the external force on the cylinders 14 and 15 is directly proportional to the difference $\Delta p = p_{ICP} - p_{ATM}$. When $p_{ICP}$ is greater than $p_{ATM}$, the magnetic slug 14 will moe upward relative to coil 12 thus changing the inductance of the coilmagnetic slug system. This in turn will cause a change in the resonant frequency of the L-C tank circuit, which is detected outside the body by an external detector system 10 described below. The coaxial cylinder 15 of non-magnetic material is attached to the ferrite and is shown here to have a stop-flange which comes against a shoulder in the frame 12 when the pressure balance $\Delta p = 0$ is attained, as shown, and this will correspond to a balanced condition frequency $f_o$ of the resonant circuit. In operation, the external pressurizer-control system will increase $p_{EXT}$ in the region 8 just above the sensor until the external detector determines that the frequency $f_o$ is reached; and thus $p_{EXT}$ equals $p_{ICP}$.

Referring to FIG. 3 means of detecting, tracking, and reading out the intracranial pressure $p_{ICP}$ are illustrated. The resonant L-C circuit in the implanted sensor 16 is coupled electromagnetically to the external detection system which comprised an antenna-oscillator 17 and a signal analyzing circuit and balance pressure detector 18. The oscillator in 17, operating typically at 10 to 100 Mega Hertz, is frequency swept at an audio rate. It experiences a power dip at the sensor's resonant frequency and the analyzer circuit 18 detects this dip and generates an output signal proportional to the associated resonant frequency. Such "grid-dip" oscillator detectors are well known and need not be described in detail here. The pressurizer-control system consists of a source of fluid 19 under pressure $p_{EXT}$ which is connected by a tube to pressure cuff 11, a pressure control means 20 for varying $p_{EXT}$ in 19 and 11, and a means 21 of measuring and reading out the pressure in 19. The pressure control means 20 would increase the pressure in 19, and thus $p_{EXT}$ applied to sensor 16 through the skin, until signal analyzer 18 detects that the frequency corresponding to a pressure balance on the sensor has been reached. At this point $p_{ICP} = p_{EXT}$ and is read out of 21. Pressure controller 20 may be manually operated or coupled to the output of 18 for automatic tracking of $p_{ICP}$. The pressure cuff 11 can be a flexible bag integrally attached to 17.

Figure 2:
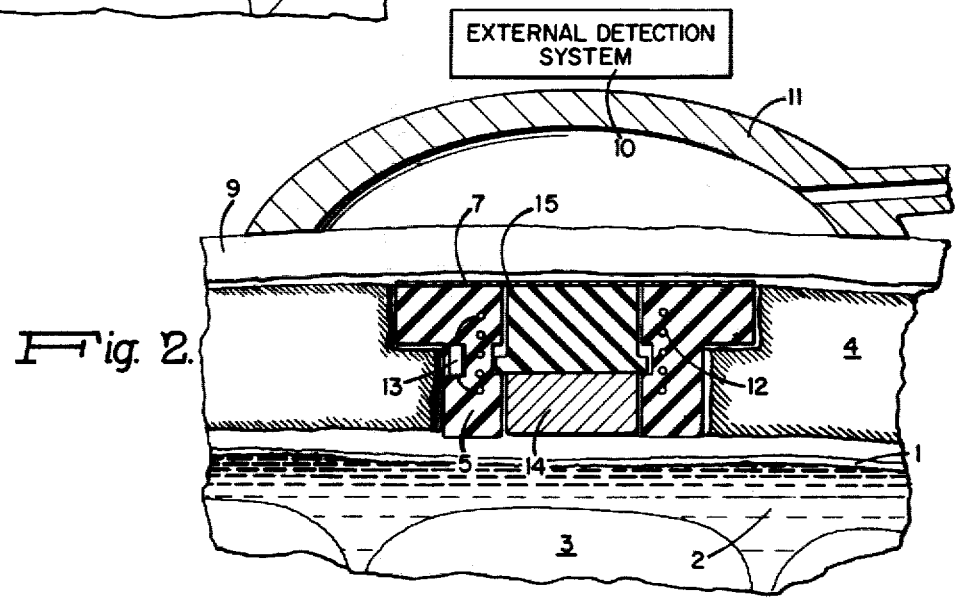
FIG. 2 shows a view in vertical section of a more specific design of the invention concept of FIG. 1 involving a passive L-C resonant circuit in the sensor.

There are several other notable novel features and ancillary points to be made about the design of FIG. 2. The novel features of the application of an external balancing pressure to the sensor through the skin and the provision of a shoulder stop of 14 and 15 against the body 5 at equilibrium position, not only allow an instant zero pressure reference check, but also insures an instant check of the operation of the entire system and correction to any temperature dependent variations in the electro-mechanical characteristics of the sensor. The coil 12 and capacitor 13 can easily be selected for negligible temperature drift and high resonant Q. The cylinders 14 and 15 can be teflon coated and axially suspended on diaphragm 7 so that friction is minimized and the static and dynamic response and sensitivity are maximized. The design has been demonstrated in implantations to detect differences in intracranical pressure of less than 5 mm of $H_2O$ and to record easily the rapid pressure variations due to heart beat and respiration, these being important clinical indications of a working system which previous designs cannot achieve. The diaphragm 7 may be arranged co-planar with the dura 1 or scalp 9, during equilibrium so that surface tension effects of the latter are eliminated and fibrosis of the dura will not occur in long implantations, a problem which has plagued previous designs. A range of clinically observed pressures can be measured with complete linearity. The sensor is cosmetically inobtrusive, lying flat with the scull 4. The design of FIG. 2 can be made less than $\frac{1}{2}$ inch in diameter and as shallow as 3 to 11 mm total height, making them adaptable to infants or small animals as well as adults. The design is intrinsically simple for high volume, low manufacture. It can be made of biocompatible material and covered with a thin silicone rubber enclosure.

Figure 1:
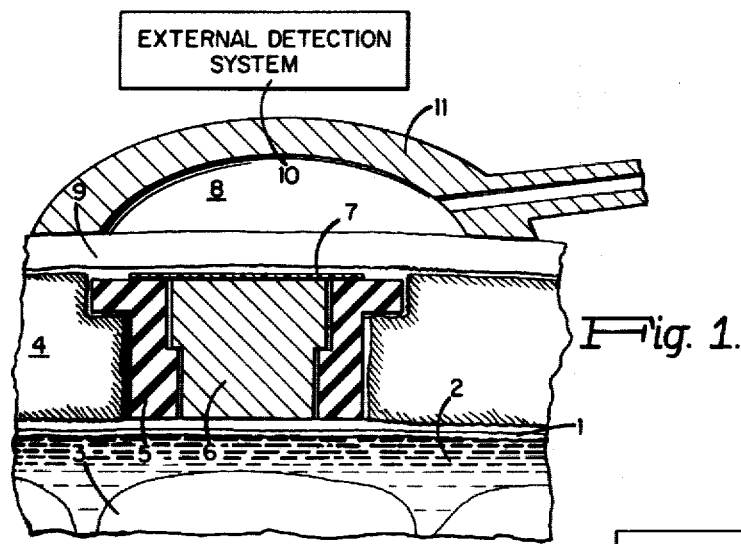
FIG. 1 shows a schematic, vertical sectional view of an implanted pressure sensor and related external systems being used to measure intracranial pressure in a living human being.
Figure 3:
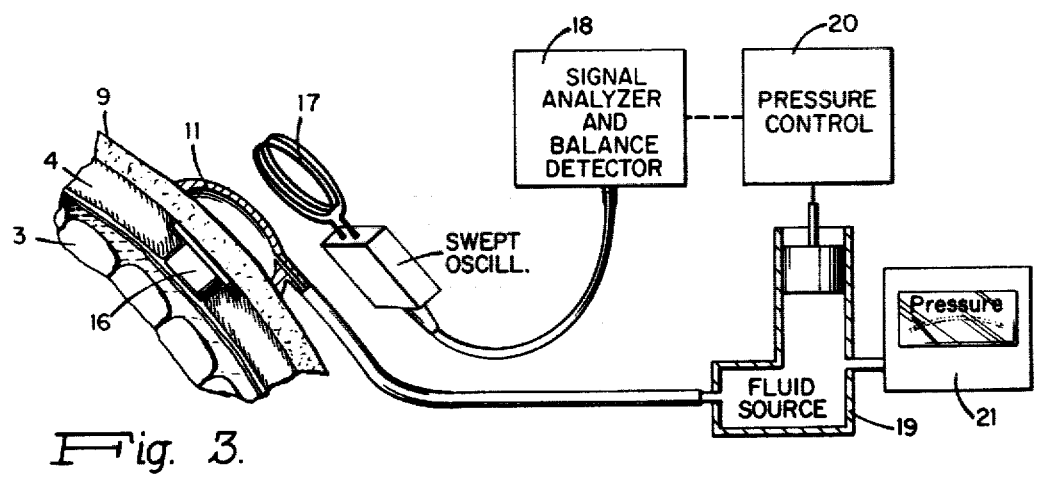
FIG. 3 illustrates implementation of the external detection and external pressurizer-control systems relative to the implanted sensor.

It is understood that many variations of the basic concepts disclosed in FIGS. 1, 2 and 3 are possible and included in this disclosure. The coupling element 6 may be a rigid mechanical means such as a cylinder or linkage, or may be a fluid transmitted through the body by a tube or channel. The physical characteristic of the sensor which is changed and detected with change of differential pressure $\Delta p = p_{ICP} - p_{EXT}$ may be diverse, and accordingly, so may be the detection means. For example, referring to FIG. 1, the body 5 and movable element 6 may be scatterers or absorbers of mechanical, acoustic, or ultrasonic waves or of electromagnetic waves such as micro waves or infrared radiation and the external detector system 10 may involve a source, interferometer, echo detector, frequency or amplitude detector of these waves by which the balance condition of 6 relative to 5 may be detected. Unlike the design of FIG. 2 the sensor may contain active circuits with stored energy cells or induction power circuits. Many variations of the passive L-C circuit system of FIGS. 2 and 3 are possible, involving other kinds of variable inductors, variable capacitors, both variable inductors and capacitors, or variable resistors to change the resonant frequency or impedance with pressure. Yet another type of electro-magnetic detection of the balance condition would be a simple pair of mechanical electric contacts which close when the $\Delta p = 0$ and opens when $\Delta p \neq 0$, thus completing a passive or active circuit which is detected externally by electromagnetic means. Wide latitude is possible in choice of geometry, size, configuration of components, coil and ferrite geometrics, and frequency of the design of FIG. 2. The magnetic slug may be replaced by a conductive metal slug to achieve induction change by eddy current detuning. The diaphragm or diaphragms may be convoluted as a speaker or rolling diaphragm or as a usual cylindrical bellows to achieve flexibility. The diaphragm may be metal or metal-coated or made of a variety of strong, impermeable, and flexible materials.

Figure 4:
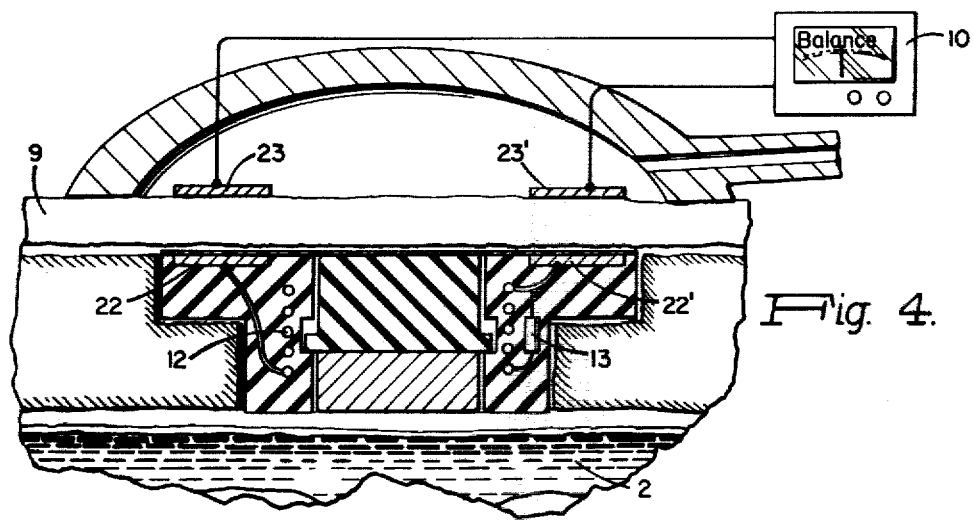
FIG. 4 illustrates capacitive transcutaneous coupling across the skin to an implanted sensor similar to that in FIG. 2.
Figure 5:
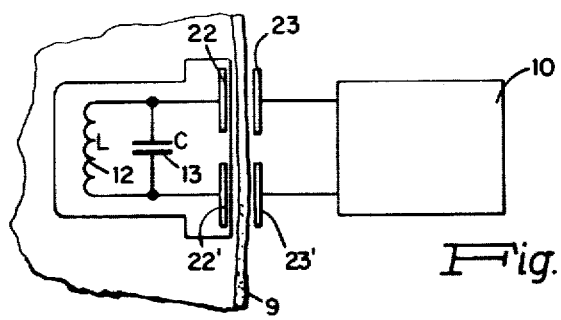
FIGS. 5, 6, 7 and 8 illustrate other sensor and transcutaneous coupling methods.

Referring to FIGS. 4 and 5, an example is shown of a sensor which incorporates an L-C resonant circuit similar to that in FIG. 2 but a different method of electromagnetic coupling across the skin 9 to the external detector system 10. The coupling method is transcutaneous capacitive coupling and is done by area electrodes 22 and 22' near the upper surface of the sensor. These are in proximity to electrodes 23 and 23', respectively, on the skin 4. At the L-C resonant frequency the capacitive reactance of these pairs of adjacent electrodes is small, and thus one can use the resonant frequency of the implanted L-C circuit to determine the frequency of oscillation of an external strongly coupled oscillator housed in 10. This frequency can then be used to indicate the pressure balance condition and the intracranial pressure as discussed above.

It is understood that variants of the transuctaneous coupling scheme of FIGS. 4 and 5 are assumed in this disclosure. For example, whereas in FIGS. 4 and 5 an inductor L and capacitor C are built into the sensor, either one of which or both of which may vary with pressure, it is also possible that only the pressure sensing inductor L, or capacitor C, may be in the implanted sensor, and that the other element of the L-C circuit, C or L respectively, may be in the external system 10 along with the strongly coupled oscillator.

Figure 6:
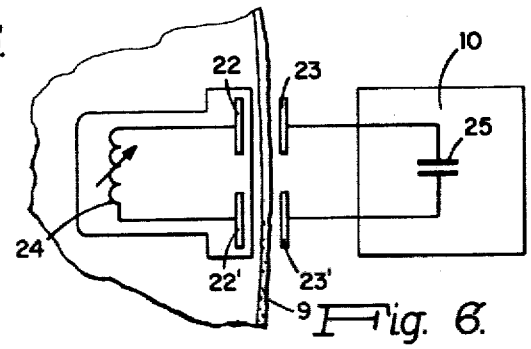

Referring to FIG. 6 the variable pressure sensing inductor 24 is coupled transcutaneously by area electrode pairs 22 and 22' and 23 and 23' to an external capacitor 25 which is integrated into the active external oscillator system that is contained in the external detection system 10. The frequency of oscillations of the external oscillator in 10 is determined by the L-C circuit made up of 24 and 25 and thus determines the balance conditions and intracranial pressure which is read out by 10.

Figure 7:
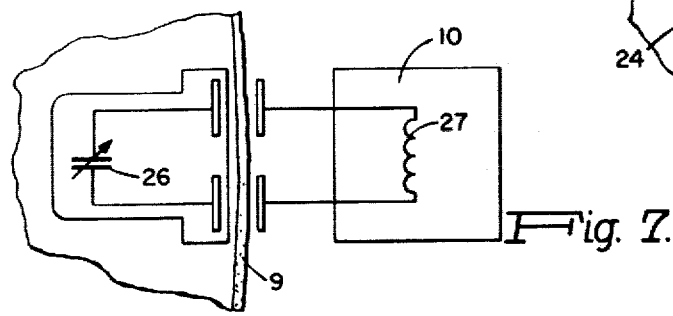

Referring to FIG. 7, the implanted sensor contains the pressure sensitive capacitor 26, and the external active oscillator in 10 contains the complementary inductor 27.

Figure 8:
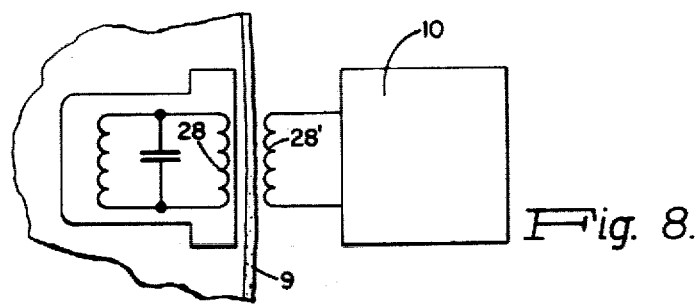
Figure 11:
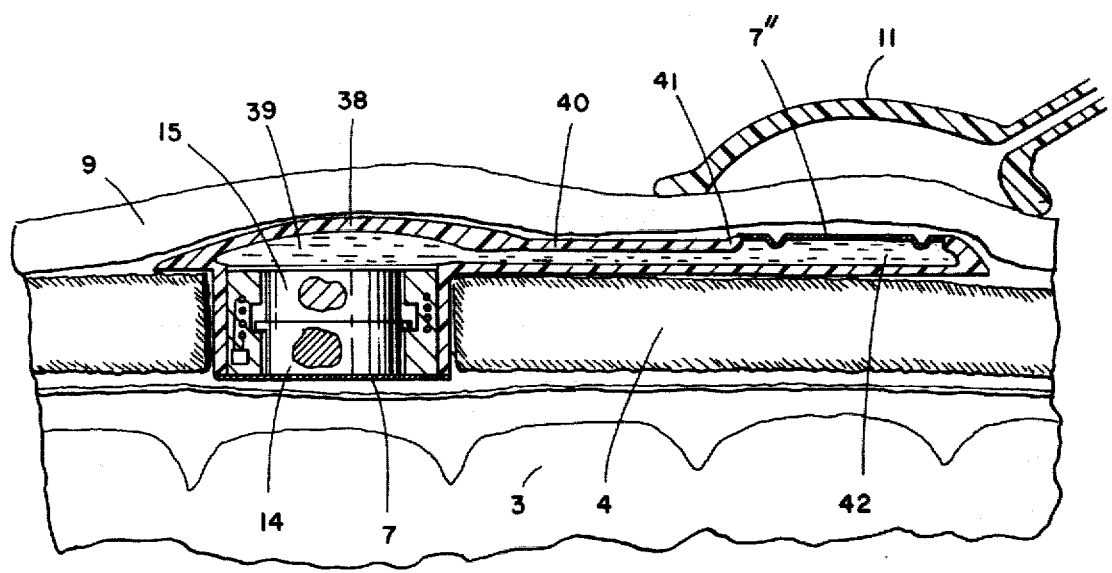

Referring to FIG. 8, the transcutaneous coupling is shown to be inductive rather than capacitive. The implanted L or C may be pressure sensitive, or the implant may contain only L or only C analogously to FIG. 6 and FIG. 7. The implanted coil 28 is coupled to external coil 28', thus achieving the necessary coupling through the skin to the external oscillator in 10. Again, as in designs of FIGS. 5, 6 and 7 the frequency of the external oscillator is determined by the L-C value of the pressure sensitive tank circuit.

Other embodiments of the basic designs disclosed above can be devised for other types of pressure measurements within the body and head. To take as illustrative examples in the case of measuring intracranial pressure, the present invention can be used in conjunction with other functional devices, such as catheters, valves, shunts, flushing devices, reservoirs, filters, anti-siphon devices, and so one, to form a more diverse or multi-purpose intracranial pressure monitoring and control system. Some important illustrations are given below.

Referring to FIG. 9, the invention is shown connected to a ventricular catheter 29, which penetrates the brain 3 to the depth of the ventrical space 30 and samples the cerebrospinal fluid 31 therein through the holes 32. This device would then measure intraventricular fluid pressure, The catheter is usually made of silicone rubber and is an integral continuation of the encapsulation of the pressure sensor. Some variations in the designs of FIGS. 1 and 2 are also included in FIG. 9. A single diaphragm 7 is used and attached to a ferrite or magnetic cylinder 14 and a thinner geometry of the coil 12 and sensor body 5. In the pressure balanced position the top of the magnetic cylinder 14 is coplanar with the outer table of the skull and its lower rim rests on a shoulder in the body 5. In operation, the hydrostatic pressure of the cerbrospinal fluid acts directly on the bottom side of this single membrane and it must be balanced by an equal external pressure applied through the pressure cuff 11, at which point the resonant L-C circuit's frequency is the balanced frequency $f_o$ as detection system 10.

Referring to FIG. 10, a sensor of low profile as in FIG. 9 is used with a catheter 29 which reaches into the ventricular space in the brain and probes the cerebrospinal fluid pressure there. This fluid presses on the membrane 7 which is attached to the magnetic slug 14.

The end of slug 14 is coplanar with the scalp in the balanced position. The cerbrospinal fluid may be channelled further through tube 33 to a fluid valve 34. Should an excess intraventricular pressure exist, the valve can be opened and the fluid shunted off into the blood stream or elsewhere through the exit tube 35. Shunt valves and ventricular catheter combinations already exist, however, the combination of these with the pressure sensor as in FIG. 10 is a new and unique combination made possible by the present invention concept. Enabling the brain pressure to be read by the sensor is an essential check on the patient status and the proper functioning of the valve. The very low profile of the sensor which is possible with this invention design is of critical importance in such implementations as in FIGS. 9 and 10. It is readily possible to automatically monitor the pressure in an arrangement like that in FIG. 10 and also automatically control the operation of the shunt valve 34 according to whether the pressure is too high or not. It is assumed that such extrapolations and combinations in usage of the present invention are included in the present disclosure.

Having described in detail various embodiment of my invention, it will now be apparent to those skilled in the art that numerous modifications can be made therein without departing from the scope of the invention as defined in the following claims. For example, external manipulation of the diaphragm can be achieved by fluidly coupling a pressure source to the diaphragm by means of a fluid filled tube extending through the skin to the diaphragm.

What I claim and desire to secure by Letters Patent of the United States is:

1. An in vivo differential pressure sensor adapted for implantation beneath the skin in the living body for in vivo calibration after implantation, said sensor comprising:

(a) a housing having means defining an opening therein;

(b) a single flexible diaphragm means which extends across the housing opening and is secured with respect to said housing, said single flexible diaphragm means having a first and a second side, at least a portion of said first side comprising at least a portion of the exterior surface of said sensor, said housing and said single flexible diaphragm means being adapted so that, when said sensor is implanted beneath the skin, the exterior surface of said single flexible diaphragm means is positioned to be adjacent to and facing an interior portion of skin whereby said exterior surface portion of said single flexible diaphragm means is in mechanical pressure communication with the skin and whereby pressures external to the body can be communicated mechanically across the skin to said single flexible diaphragm means;

(c) means allowing the second side of said single flexible diaphragm means to be in contact with and in mechanical pressure communication with a bodily medium, the pressure of which is to be sensed when said sensor is implanted in the living body, so that changes in the difference of pressures on said two sides of said single flexible diaphragm means cause a motion of at least a portion of said single flexible diaphragm means (d) means connected to said housing for contacting the single flexible diaphragm means for a predetermined relationship between the pressures on said single flexible diaphragm means thereby defining a mechanical contact reference position of said single flexible diaphragm means with respect to said housing for a predetermined relationship between the pressures on said single flexible diaphragm means; and, (e) means having a preselected parameter that is detectable by detection apparatus located outside the living body, said means having a preselected parameter being at least in part cooperatively connected to and movable with said single flexible diaphragm means so that preselected parameter will change with movement of said single flexible diaphragm means, said parameter being detectable at least when said single flexible diaphram means is substantially at said mechanical contact reference position and said parameter changing upon at least a displacement of at least: (i) a portion of said single flexible diaphragm means from said mechnical contact reference position or (ii) displacements of at least a portion of said single flexible diaphragm means with respect to said housing; whereby when said sensor is implanted beneath the skin said single flexible diaphragm means can be driven to said mechanical contact reference position by a pressure external to the living body applied to the skin adjacent to said sensor and said preselected parameter can be determined at said mechanical contact reference position after implantation and whereby the magnitude of the external pressure applied to the skin that is required to drive said single flexible diaphragm means to said mechanical contact reference position is a function of the pressure in said bodily medium.

2. The sensor of claim 1 wherein said means allowing said second side of said single flexible diaphragm means to contact a second bodily medium comprises a through opening in said housing, with said single flexible diaphragm means extending across said through opening and being secured with respect to said housing.

3. An in vivo differential pressure sensor adapted for implantation beneath the skin in the living body and sensing the pressure of a bodily fluid and adapted for in vivo calibration after implantation, said sensor comprising:

(a) a housing;

(b) a single flexible diaphragm means which is fluid pressure sealed with respect to said housing and having a first and a second side with at least a portion of said first side comprising at least a portion of the exterior surface of said sensor and being positioned so that after implantation, said portion of said first side is in mechanical pressure communication with the skin and whereby pressures external to the body can be communicated mechanically across the skin to said single flexible diaphragm means, said single flexible diaphragm means and said housing together defining a chamber such that the second side of said single flexible diaphragm means communicates mechanically with pressure inside said chamber so that changes in the difference in pressures on said two sides of said single flexible diaphragm means causes a motion of at least a portion of said single flexible diaphragm means;

(c) inlet means to said chamber allowing the entrance of a bodily fluid from an internal bodily region to the inside of said chamber, thereby providing a fluid pressure communication between said internal bodily region and the inside of said chamber when said sensor is implanted in the living body, and enabling that a change in the pressure in said internal bodily region will cause a movement of at least a portion of said single flexible diaphragm means with respect to said housing;

(d) contact means connected to said housing for contacting the single flexible diaphragm means for a predetermined relationship between the pressures on said single flexible diaphragm means thereby defining a mechanical contact reference position of said single flexible diaphragm means with respect to said housing at a predetermined relationship between said pressures on said single flexible diaphragm means;

(e) means having a preselected parameter that is detectable by detection apparatus located outside the living body, said means having a preselected parameter being at least in part cooperatively connected to and movable with said single flexible diaphragm means so that said preselected parameter will change with movement of said single flexible diaphragm means, said parameter being detectable at least when said single flexible diaphragm means is at said mechanical contact reference position and said parameter changing upon at least: (i) a displacement of at least a portion of said single flexible diaphragm means from said mechanical contact reference position or (ii) displacements of at least a portion of said single flexible diaphragm means with respect to said housing; whereby when said sensor is implanted beneath the skin, said single flexible diaphragm means can be driven to said mechanical contact reference position by a pressure external to the living body applied to the skin adjacent to said sensor and said preselected parameter can be determined at said mechanical contact reference position by a pressure external to the living body applied to the skin adjacent to said sensor and said preselected parameter can be determined at said mechanical contact reference position after implantation, and whereby the magnitude of the external pressure applied to the skin required to drive said single flexible diaphragm means to said mechanical contact reference position is a function of the pressure in said internal bodily region.

4. The apparatus of claim 3 wherein said housing has an opening in its walls and is fluid pressure sealed with respect to said housing so that said single flexible diaphragm means defines part of the exterior surface of said sensor.

5. The apparatus of claim 3 wherein said contact means comprises a mechanical stop means which stops the motion of said movable portion of said single flexible diaphragm means with respect to said housing at said predetermined pressure relationship.

6. The apparatus of claim 3 wherein said contact means includes electrode contacts that change their electrical condition at a reference position of said single flexible diaphragm means relative to said housing, and said means having a detectable parameter includes circuit means within said sensor and cooperative with said electrode contact whereby the change in electrical condition of said electrode contacts produces a characteristics response of said circuit that is detectable by apparatus outside said living body.

7. The apparatus of claim 3 wherein said contact means is so adapted that said mechanical contact reference position corresponds to the balance of said pressures on opposite sides of said single flexible diaphragm means.

8. The apparatus of claim 3 wherein said inlet means comprises a tube.

9. The apparatus of claim 3 wherein the locus of points where said single flexible diaphragm means is fluid pressure sealed to said housing defines a perimeter which lies substantially in a plane, and wherein said single flexible diaphragm means is at least partially in coplanar geometry with respect to said plane for said predetermined pressure relationship.

10. The apparatus of claim 3 wherein said means having a preselected, detectable parameter comprises electronic circuit means, said parameter being a characteristic response parameter of said circuit means which is detectable by electromagnetic coupling to electronic apparatus means located external to said living body.

11. The apparatus of claim 10 wherein said electronic circuit means includes an inductor and further comprises a magnetic material that is cooperatively connected to said single flexible diaphragm means and which which moves relative to the inductor with at least a portion of said single flexible diaphragm means, such movement producing a displacement of said magnetic material relative to said inductor thereby varying the inductance of said inductor.

12. The apparatus of claim 10 wherein said electronic circuit means includes an inductor and further comprises a conductive material that is cooperatively connected to said single flexible diaphragm means and which moves relative to the inductor with at least a portion of said single flexible diaphragm means, such movement producing a displacement of said conductive material relative to said inductor thereby varying the inductance of said inductor.

13. The apparatus of claim 10 wherein said electronic circuit means comprises a resonant electrical circuit which includes a coil and a capacitor.

14. The apparatus of claim 13 wherein said coil is fixed with respect to said housing.

15. The apparatus of claim 13 further comprising means for varying the capacitance of said capacitor in response to said displacement of at least a portion of said single flexible diaphragm means.

16. The apparatus of claim 13 wherein said resonant electrical circuit is a parallel resonant circuit and wherein said preselected detectable parameter is the resonant frequency of said resonant circuit.

17. The apparatus of claim 3 wherein said single flexible diaphragm means is spring loaded with respect to said housing.

18. The apparatus of claim 3 and further comprising an outlet means which permits the exit of fluid from the interior of said chamber.

19. The apparatus of claim 18 wherein said inlet and outlet means include tubes.

20. The apparatus of claim 18 further comprising a fluid shunt valve means interposed in series with at least one of said inlet or said outlet means for regulating the flow of said bodily fluid from said second bodily region.

21. The apparatus of claim 18 further comprising a fluid shunt valve means which is mounted in part of said single flexible diaphragm means and in part on said housing so that at least a portion of said single flexible diaphragm means displaces under changes in said pressures on either side of said single flexible diaphragm means, there will result a change in the opening of said fluid shunt valve means so as to change the flow regulation of said bodily fluid.

22. The apparatus of claim 3 wherein the part of said means having a preselected, detectable parameter that is cooperatively connected to said single flexible diaphragm means is at least a part of said single flexible diaphragm means.

23. The sensor of claim 3 wherein said means having a preselected, detectable parameter comprises a scatterer of ultrasonic radiation.

24. An in vivo differential pressure sensor adapted for implantation in the living body and adapted for in vivo calibration after implantation and sensing the pressure of a bodily fluid, said sensor comprising;

(a) a housing having means defining an opening therein;

(b) a single flexible diaphragm means extending over the end of the housing opening and being fluid pressure sealed with respect to said housing, said single flexible diaphragm means forming part of the exterior surface of the sensor whereby when said sensor is implanted beneath the skin, said single flexible diaphragm means is adjacent to and in pressure communication with the skin and whereby pressure external to the body applied to the skin is mechanically communicated to said single flexible diaphragm means, said single flexible diaphragm means and said housing forming a chamber with said single flexible diaphragm means communicating on one side with pressure inside the chamber and on the other side with pressure external to the sensor and adjacent to said single flexible diaphragm means;

(c) inlet means to said chamber allowing the entrance of a bodily fluid from an internal bodily region to the inside of said chamber and thereby proving fluid pressure communication between said internal bodily region and said single flexible diaphragm so that a change in the difference of pressures on said single flexible diaphragm means will produce a movement of a portion of said single flexible diaphragm means with respect to said housing;

(d) a magnetic material that is connected to and thus moves with said single flexible diaphragm means;

(e) a parallel resonant circuit means comprising an inductor and a capacitor that are mounted within said housing so that the inductance of said inductor and thus the resonant frequency of said resonant circuit is varied in accordance with the position of the magnetic material relative to the inductor, said resonant frequency being detectable by apparatus external to the living body;

(f) a mechanical stop for said single flexible diaphragm means against said housing when the pressure external to said sensor on said single flexible diaphragm means is equal to or greater than the pressure in said chamber whereby, when said sensor is implanted beneath the skin, said single flexible diaphgram means can be driven to said mechanical stop by a pressure applied externally to the skin and said resonant frequency can be determined at said mechanical stop after implantation and whereby the magnitude of the external pressure applied to the skin required to drive said single flexible diaphragm means to said mechanical stop is a measure of the pressure of said bodily fluid.

25. The sensor of claim 24 and further comprising an outlet means for allowing said bodily fluid to flow out of said chamber, the outlet means including a tubing.

26. The sensor of claim 25 and further comprising a fluid shunt valve means in series arrangement with at least one of said inlet or said outlet means so as to regulate the flow of said bodily fluid.

27. The sensor of claim 25 and further comprising a fluid reservoir in series with at least one of said inlet or said outlet means.

28. An in vivo differential pressure sensor adapted for implantation in the living body and adapted for in vivo calibration after implantation and sensing the pressure of a bodily fluid, said sensor comprising:

(a) a housing having means defining an opening therein;

(b) a single flexible diaphragm means extending over the end of the housing opening and being fluid pressure sealed with respect to said housing, said single flexible diaphragm means forming part of the exterior surface of the sensor whereby when said sensor is implanted beneath the skin said single flexible diaphragm means is adjacent to and in pressure communication with the skin and whereby pressure external to the body applied to the skin is mechanically communicated to said single flexible diaphragm means, said single flexible diaphragm means and said housing forming a chamber with said single flexible diaphragm means communicating on one side with pressure inside said chamber and on the other side with pressure external to said sensor and adjacent to said single flexible diaphragm means;

(c) inlet means to said chamber allowing the entrance of a bodily fluid from an internal bodily region to the inside of said chamber and thereby proving fluid pressure communication between said internal bodily region and said single flexible diaphragm means so that a change in the difference of pressure or said single flexible diaphragm means will produce a movement of a portion of said flexible diaphragm means with respect to said housing;

(d) a conductive material that is connected to and thus moves with said single flexible diaphragm means;

(e) a parallel resonant circuit means comprising an inductor and a capacitor that are mounted within said housing so that the inductance of said inductor and thus the resonant frequency of said resonant circuit is varied in accordance with the postion of the conductive material relative to the inductor, said resonant frequency being detectable by apparatus external to the living body;

(f) a mechanical stop for said single flexible diaphragm means against said housing when pressure external to said sensor on said single flexible diaphragm means is equal to or greater than the pressure in said chamber whereby, when said sensor is implanted beneath the skin, said single flexible diaphragm means can be driven to said mechanical stop by a pressure applied externally to the skin and said resonant frequency be determined at said mechanical stop after implantation and whereby the magnitude of the external pressure applied to the skin required to drive said single flexible diaphragm means to said mechanical stop is a measure of pressure of said bodily fluid.

29. The sensor of claim 28 and further comprising an outlet means for allowing said bodily fluid to flow out of said chamber, the outlet means including a tubing.

30. The sensor of claim 28 and further comprising a fluid shunt valve means in series arrangement with at least one of said inlet or said outlet means so as to regulate the flow of said bodily fluid.

31. The sensor of claim 28 and further comprising a fluid reservoir in series with either said inlet or said outlet means.

32. An in vivo pressure detecting system comprising in combination:

(a) a differential pressure sensor adapted for implantation in a living body and for in vivo calibration after implantation, said sensor comprising;

(1) a housing having means defining an opening therein;

(2) a single flexible diaphragm means which extends across the housing opening and is secured with respect to said housing, said single flexible diaphragm means having a first and a second side, at least a portion of said first side comprising at least a portion of the exterior surface of said sensor, said housing and said single flexible diaphragm means being adapted so that when said sensor is implanted beneath the skin, the exterior surface of said single flexible diaphragm means is positioned to be adjacent to and facing an interior portion of skin whereby said exterior surface portion of said single flexible diaphragm means is in mechanical pressure communication with the skin and whereby pressures external to the body can be communicated mechanically across the skin to said single flexible diaphragm means;

(3) means allowing the second side of said single flexible diaphragm means to be in contact, and thereby in pressure communication with a bodily medium the pressure of which is to be sensed when said sensor is implanted in the living body, so that changes in the difference in pressures on said two sides of said flexible diaphragm means cause motion of at least a portion of said single flexible diaphragm means with respect to said housing;

(4) means connected to said housing for contacting the single flexible diaphragm means for a predetermined relationship between the pressures on said single flexible diaphragm means thereby defining a mechanical contact reference position of said single flexible diaphragm means with respect to said housing for a predetermined relationship between said pressures on said single flexible diaphragm means;

(5) means having a preselected parameter that is detectable by detection apparatus located outside the living body, said means having a preselected parameter being at least in part cooperatively connected to and movable with said single flexible diaphragm means so that said preselected parameter will change with movement of said single flexible diaphragm means, said parameter being detectable at least when said single flexible diaphragm means is substantially at said mechanical contact reference position and said parameter changing upon at least: (i) a displacement of at least a portion of said single flexible diaphragm means from said mechanical contact reference position or (ii) displacement of at least a portion of said single flexible diaphragm means with respect to said housing; whereby when said sensor is implanted beneath the skin said single flexible diaphragm means can be driven to said mechanical contact reference position by a pressure external to the living body applied to the skin adjacent to said sensor and said preselected parameter can be determined at said mechanical contact reference position after implantation and whereby the magnitude of the external pressure applied to the skin required to drive said single flexible diaphragm means to said mechanical contact reference position is a function of the pressure in said bodily medium;

(b) a controllable pressure source means adapted to be located external to the living body and in cooperative relation with the living body and said single flexible diaphragm means for establishing said predetermined pressure relationship; and, (c) means for detecting said preselected parameter and the value of said preselected parameter at said mechanical contact reference position and any variation therefrom when said sensor is implanted in a living body, said detecting means being adapted to be located external to the living body and in cooperative relation with the living body and said sensor and without any connection to said sensor which requires a break in the skin of the living body.

33. The system of claim 32 wherein at least a portion of said controllable pressure source means and said sensor parameter detecting means comprise an integral unit.

34. An in vivo pressure detecting system comprising in combination:

(a) an in vivo differential pressure sensor adapted for implantation beneath the skin in the living body and sensing the pressure of a bodily fluid, and adapted for in vivo calibration after implantation, said sensor comprising:

(1) a housing;

(2) a single flexible diaphragm means which is fluid pressure sealed with respect to said housing and has a first and a second side with at least a portion of said first side comprising at least a portion of the exterior surface of said sensor and being positioned so that after implantation, said portion of said first side is in mechanical pressure communication with the skin and whereby pressures external to the body can be communicated mechanically across the skin to said single flexible diaphragm means, said single flexible diaphragm means and said housing together defining a chamber such that the second side of said single flexible diaphragm means communicates mechanically with pressure inside said chamber so that changes in the difference in pressures on said two sides of said single flexible diaphragm means cause a motion of at least a portion of said single flexible diaphragm means;

(3) inlet means to said chamber allowing the entrance of a bodily fluid from an internal bodily region to the inside of said chamber when said sensor is implanted in the living body, thereby providing a fluid pressure communication between said internal bodily region and the inside of said chamber when said sensor is implanted in the living body, and enabling that a change in pressure will cause a movement of at least a portion of said single flexible diaphragm means with respect to said housing;

(4) contact means connected to said housing for contacting the single flexible diaphragm means for a predetermined relationship between the pressures on said single flexible diaphragm means thereby defining a mechanical contact reference position of said single flexible diaphragm means with respect to said housing at a predetermined relationship between said pressures on said single flexible diaphragm means;

(5) means having a preselected parameter that is detectable by detection apparatus located outside the living body, said means having a preselected parameter being at least in part cooperatively connected to and movable with said single flexible diaphragm means so that said preselected parameter will change with movement of said single flexible diaphragm means, said preselected parameter being detectable at least when said single flexible diaphragm means is at said mechanical contact reference position and said parameter changing upon at least: (i) a displacement of at least a portion of said single flexible diaphragm means from said mechanical contact reference position or (ii) displacement of at least a portion of said single flexible diaphragm means with respect to said housing; whereby when said sensor is implanted beneath the skin said single flexible diaphragm means can be driven to said mechanical contact reference position by a pressure external to the living body applied to the skin adjacent to said sensor and said preselected parameter can be determined at said mechanical contact reference position after implantation and whereby the magnitude of the external pressure applied to the skin required to drive said single flexible diaphragm means to said mechanical contact reference position is a function of the pressure of said bodily fluid;

(b) a controllable pressure source means adapted to be located external to the living body and in cooperative relation with the living body and said single flexible diaphragm means for establishing said predetermined pressure relationship; and, (c) means for detecting said preselected parameter and the value of the parameter at said mechanical contact reference position and any variation therefrom when said sensor is implanted in a living body, said detecting means being adapted to be located external to the living body and in cooperative relation with the livig body and said sensor and without any connection to said sensor which requires a break in the skin of the living body.

35. The system of claim 34 wherein at least a portion of said controllable pressure sources means and said sensor parameter detecting means comprise an integral unit.

36. An in vivo differential pressure sensor adapted for implantation in the living body, said sensor comprising:

(a) a housing having means defining an opening extending therethrough;

(b) a single flexible diaphragm means extending across said housing opening and secured to said housing, said single flexible diaphragm means communicating with pressures in two separate regions external to the sensor that are separated by the single flexible diaphragm means with the pressure in one of the regions being an internal bodily pressure when the sensor is implanted in a living body so that opposite sides of said single flexible diaphragm means are in contact with and in mechanical pressure communication with two bodily media that are separated by said single flexible diaphragm means;

(c) contact means connected to said housing for contacting the single flexible diaphragm means for a predetermined relationship between the pressure on said single flexible diaphragm means thereby defining a mechanical contact reference position of said single flexible diaphragm means with respect to said housing for a predetermined pressure relationship in said regions; and, (d) means having a preselected, detectable parameter that changes upon at least a displacement from said mechanical contact reference position of said single flexible diaphragm means upon a change from said predetermined pressure relationship.

37. An in vivo differential pressure sensor adapted for in vivo calibration after implantation, said sensor comprising:

(a) a housing which defines a chamber therein, at least a portion of the wall of said housing being flexible so that changes in the pressures inside said chamber and outside said housing will cause movement of said flexible portion of said housing wall, said housing being adapted so that, when implanted beneath the skin in the living body, said flexible portion of said housing wall can be placed in mechanical pressure communication with an interior portion of skin and whereby pressures external to the body can be communicated mechanically across the skin to said flexible portion of said housing wall;

(b) inlet means to said chamber allowing the entrance into said chamber of a bodily fluid, the pressure of which is to be measured when the sensor is implanted in the body;

(c) stop means within said housing adapted to make contact with, and thereby stop the movement of, said flexible portion of said housing wall for a predetermined pressure relationship between pressures inside said chamber and outside said housing;

(d) means within said housing having a preselected parameter that is detectable by apparatus outside the living body, said means having a preselected parameter being at least in part cooperatively connected to said flexible portion of said housing wall so that said preselected parameter will change with the movement of said flexible portion of housing wall, the preselected parameter being detectable at least when said flexible portion of the wall is in contact with said stop means and said parameter changing upon at least a movement of said flexible portion of wall away from said stop means, whereby when said sensor is implanted beneath the skin, said flexible portion of wall can be driven to contact said stop means by a pressure external to the living body applied to the skin adjacent to said sensor and said preselected parameter can be determined when said flexible portion of the wall is in contact with said stop means after implantation, and whereby the magnitude of the external pressure applied to the skin required to drive said flexible portion of wall to contact said stop means is a function of the pressure in said internal bodily region.

38. The sensor of claim 37 wherein said means having a preselected parameter comprises electronic circuit means with said preselected parameter being a characteristic response parameter of said electronic circuit means which is detectable by electromagnetic coupling to the electronic apparatus located external to said living body.

39. The sensor of claim 38 wherein said electronic circuit means is a resonant electronic circuit with an element of said resonant electronic circuit being at least in part cooperatively connected to said flexible portion of wall so that a movement of said flexible portion of wall will cause a change in said resonant frequency.

40. The sensor of claim 37 wherein said flexible portion of wall contacts said stop means when said pressure outside said housing on said flexible wall portion is equal to or greater than the pressure in said chamber.

* * * * *